(12) United States Patent
Netzer

(10) Patent No.: US 6,177,600 B1
(45) Date of Patent: *Jan. 23, 2001

(54) COMBINATION PROCESS FOR MANUFACTURING ETHYLENE, BENZENE AND ALKYLATED BENZENE

(76) Inventor: David Netzer, 1138 Hacienda Ct., Los Angeles, CA (US) 90069

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 09/209,638

(22) Filed: Dec. 10, 1998

Related U.S. Application Data

(63) Continuation-in-part of application No. 08/957,252, filed on Oct. 24, 1997, now Pat. No. 5,880,320, which is a continuation-in-part of application No. 08/906,381, filed on Aug. 5, 1997, now abandoned.

(51) Int. Cl.[7] .............................. C07C 1/00; C07C 2/00; C07C 4/00; C07C 5/00; C07C 6/00; C07C 2/64; C07C 15/067

(52) U.S. Cl. ........................... 585/323; 585/446; 585/448

(58) Field of Search .................... 585/446, 448, 585/323

(56) References Cited

U.S. PATENT DOCUMENTS

| | | | |
|---|---|---|---|
| 3,966,833 | * | 6/1976 | Cosyns et al. ............... 260/672 R |
| 4,009,217 | * | 2/1977 | Uitti ............................ 260/669 R |
| 4,022,847 | * | 5/1977 | McClure ...................... 260/683.68 |
| 4,107,224 | * | 8/1978 | Dwyer ......................... 260/671 R |
| 4,150,061 | * | 4/1979 | Feinstein et al. ............ 260/672 T |
| 4,167,533 | * | 9/1979 | Raymont ...................... 585/251 |
| 4,496,784 | * | 1/1985 | Moorehead ..................... 85/486 |
| 4,499,316 | * | 2/1985 | Garska et al. ................. 585/415 |
| 4,560,820 | * | 12/1985 | Field ............................ 585/489 |
| 4,720,293 | * | 1/1988 | Rolles et al. ................... 62/24 |
| 4,891,458 | | 1/1990 | Innes et al. .................... 585/323 |
| 5,176,883 | | 1/1993 | Smith, Jr. et al. ............ 422/211 |
| 5,463,154 | * | 10/1995 | Slim et al. .................... 585/261 |
| 5,675,054 | * | 10/1997 | Manley et al. ................ 585/809 |
| 5,750,814 | * | 5/1998 | Grootjans et al. ............. 585/323 |
| 5,880,320 | * | 3/1999 | Netzer .......................... 585/448 |

FOREIGN PATENT DOCUMENTS

WO9809928    3/1998   (WO).

OTHER PUBLICATIONS

Netzer, D., "Economically Recover Olefins From FCC Off-gases," *Hydrocarbon Processing*, pp. 83–91, Apr. 1997.

\* cited by examiner

*Primary Examiner*—Walter D. Griffin
*Assistant Examiner*—Thuan D. Dang
(74) *Attorney, Agent, or Firm*—Christie, Parker & Hale, LLP

(57) ABSTRACT

Gas and liquid products of an ethylene plant, steam cracking zone, are used for the coproduction of alkylated benzene. Dilute ethylene in typical concentrations of 7–20 mol percent is coproduced along with pure ethylene product. Impure benzene containing typically less than 8 wt % C6 and C7 non-aromatics is formed by hydratreating and fractionation of pyrolysis gasoline, rich in benzene and toluene, and also by hydrodealkylation of the toluene. The impure benzene reacts with dilute ethylene to form ethylbenzene and hydrogen rich vent gas. The impure benzene can be also a source for production of cumene, by reaction with propylene.

12 Claims, 5 Drawing Sheets

COMBINATION PROCESS FOR MANUFACTURING ETHYLENE, BENZENE AND ALKYLATED BENZENE

CROSS REFERENCE TO RELATED APPLICATIONS

This application is a continuation-in-part of U.S. application Ser. No. 08/957,252, filed Oct. 24, 1997, now U.S. Pat. No. 5,880,320, which is a continuation-in-part of U.S. application Ser. No. 08/906,381, filed Aug. 5, 1997, now abandoned.

FIELD OF INVENTION

The present invention is directed to an improved process for the production of ethylene and benzene for use in an adjacent or remote production of alkylated benzene.

BACKGROUND OF THE INVENTION

Conventional ethylene production consists of the following key process operation:

(a) Thermal cracking of hydrocarbons in presence of dilution steam, of $C_2+$ hydrocarbon at about 15–25 psig and 1,500–1,600° F. to form cracked gas containing ethylene in an amount of 25–40 wt % (with the exception of ethane feed), and other by products such as propylene, acetylene, hydrogen, methane and $C_3+$ products. The thermal section includes cracked gas cooling, steam generation and $C_9+$ hydrocarbon condensation. Traces of CO, $CO_2$ and $H_2S$ are formed in the cracking.

(b) Cracked gas compression to 400–600 psig, traces of $CO_2$ and $H_2S$ removal, drying, and bulk $C_4+$ product recovery by condensation at about 100° F., using cooling water.

(c) Acetylene conversion to ethylene via selective hydrogenation, chill down and cryogenic recovery of ethylene by fractionation at below −30° F.

(d) Recovery of propylene, propane and $C_4+$ hydrocarbons by warm distillation at above 80° F.

(e) Cascade refrigeration of ethylene and propylene refrigerants, to support the above, down to a temperature of below −100° F.

(f) Methane refrigeration and or turbo expander to reach refrigeration below −180° F.

(g) In case of Naphtha feed, and to a lesser extent with propane/butane feed, residual liquid products from cracking such as pyrolysis fuel oil and pyrolysis gasoline, which are rich in aromatics, are selectively hydrotreated for di-olefin and olefin saturation.

(h) Benzene/toluene and xylene (BTX) are extracted from the hydrotreated pyrolysis gasoline, and toluene is fractionated and converted to benzene by hydrodealkylation.

Efficient cryogenic recovery of the ethylene is a key element in design of ethylene plants. The motive power for compression and refrigeration, and consequently the capital cost escalates rapidly as the rate of ethylene recovery increases. For example, the typical ethylene recovery of 99.7–99.9% requires much higher investment and 50% more refrigeration energy in the demethanizer as compared with 95% rate of ethylene recovery. Thus, reduction of the marginal refrigeration required for ethylene recovery by using 95% or lower recovery could substantially improve the overall economics of the ethylene plant, if a down stream outlet, other than fuel gas, is found for the 5% more of the unrecovered gaseous ethylene. Normally the unrecovered ethylene 0.1–0.3% is routed with the methane to the fuel gas system. However, the value of ethylene as fuel is only about 15–20% of its equivalent value as downstream product. The ethylene product is commonly used as a feedstock to many downstream processing including ethylbenzene. Production of ethylbenzene from pure ethylene against dilute ethylene feed, although somewhat advantageous from a stand point of the ethylbenzene plant alone, is not an absolute requirement and its relative cost impact is rather marginal as compared with the estimated saving in the ethylene plant.

SUMMARY OF THE INVENTION

If ethylbenzene is produced at an adjacent facility, dilute ethylene at concentrations of about 3 to about 40 vol % and substantially free of propylene can be extracted from a cryogenic demethanizer as an overhead gas. The bulk of the dilute ethylene stream comprises methane and hydrogen. The dilute ethylene stream at a typical pressure of about 330 to about 500 psig and after cold recovery and acetylene removal is the feed, along with common specification benzene, 99.9% wt % purity, or impure benzene, 95 to 98 wt % purity, to an ethylbenzene plant. The ethylbenzene is normally converted to styrene.

When naphtha or heavier feeds are used, a pyrolysis gasoline product which is rich in benzene is used as a source of benzene for the ethylbenzene plant. Toluene is fractionated and converted by hydrodealkylation to benzene and methane. Thermal hydrodealkylation in the steam cracking furnace along with co-production of ethylene is a part of the invention. The benzene and co-boilers, cyclohexane and dimethylpentanes, are used as a feed to the ethylbenzene plant. The saturated $C_6$–$C_7$ co-boilers are purged from the ethylbenzene plant, alkylation reaction loop.

The benzene, along with the co-boilers, can be used also for the production of iso-propylbenzene (cumene) by reaction with propylene. The saturated $C_6$–$C_7$ co-boilers would be purged from the cumene plant alkylation loop in a similar fashion.

The invention is applicable to situations where the alkylated benzene plant is remote to ethylene production, and ethylene feed via pipeline is the mode of operation. In this case, no practical option exists for using dilute ethylene feed.

DETAILED DESCRIPTION OF THE INVENTION

For illustration and process consistency, the invention will be described for an ethylene plant when naphtha is the sole feedstock followed by ethylbenzene production. This enables demonstration of all the elements of the invention. This is reasonable since more than 60% of the world's ethylene production capacity originates from naphtha and heavier feeds.

The assumed capacity of the ethylene plant for consistency purposes is 1,000,000,000 lb/year, along with co-production of 400,000,000 lb/year of propylene, 280,000,000 lb/year of impure benzene (95 wt % benzene) and by products such as hydrogen, pyrolysis gasoline and pyrolysis fuel oil. About 8,300 hours per year of operation are assumed. Pyrolysis products such as ethane, propane, $C_4$ and $C_5$ are internally recycled and converted to ethylene and propylene. Acetylene is selectively hydrogenated to ethylene, and methylacetylene and ropadiene are selectively hydrogenated to propylene.

According to the invention, for illustrative purposes about 15% of the crude ethylene originated in the cracking, is recovered as a dilute ethylene product at a concentration of about 10.0 vol. % and serves as a feed for production of 550,000,000 lb/year of ethylbenzene at an adjacent facility.

The cracking yield is based on of molecular weight of 92, a specific gravity of about 0.69, paraffin content of about 80 wt % (50% normal, 50% iso), naphthene content of about 10 wt % and aromatic content of 10 wt %. The naphtha contains less than 0.1 wt % olefins and traces of sulfur.

Figure 1:
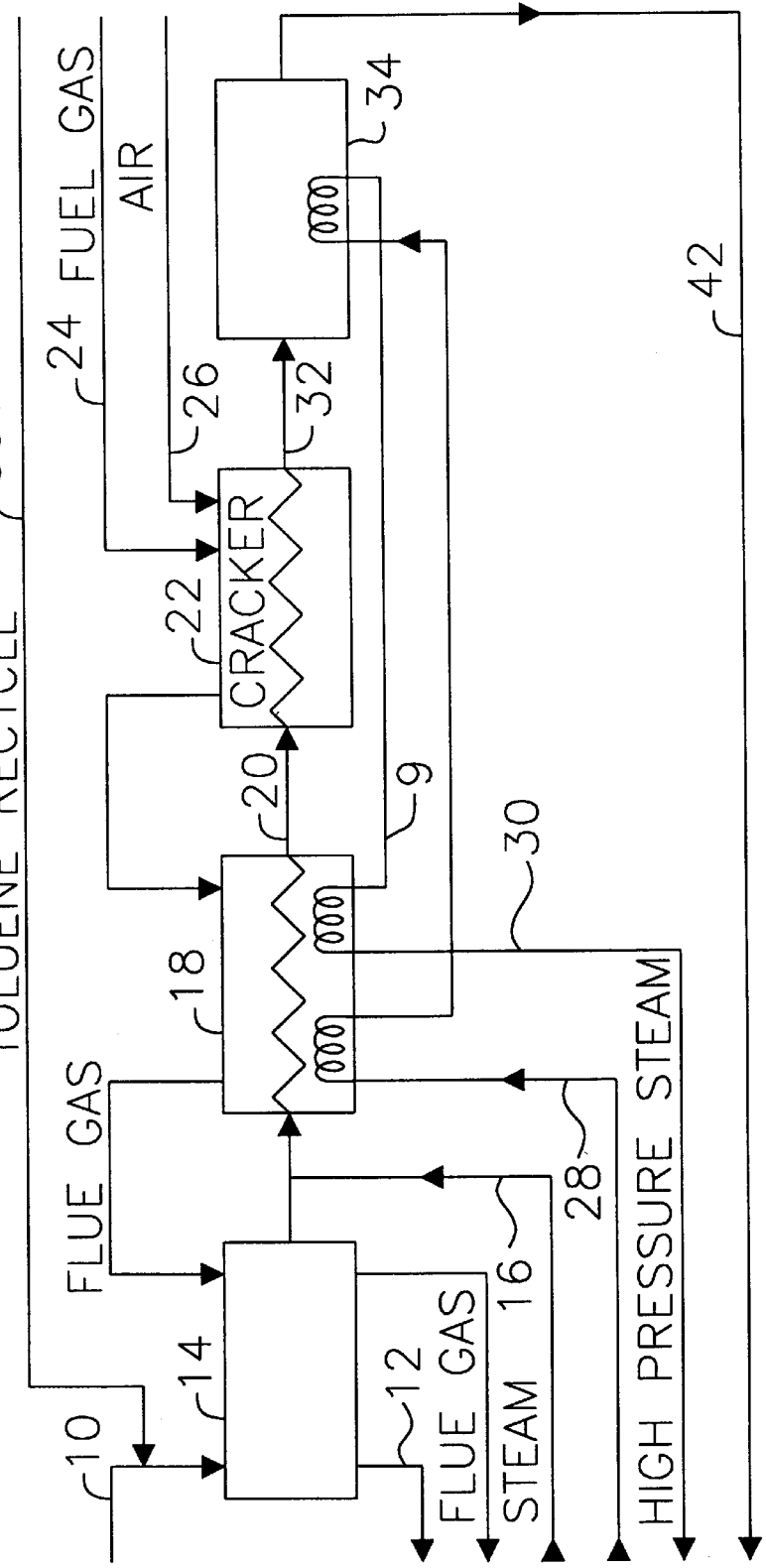
FIG. 1 illustrates the cracking section of the ethylene plant and heat recovery with high pressure steam generation and superheating.

With reference now to FIG. 1, Naphtha net feed, 10 about 33,000 bpsd (331,000 lb/hr) and about 65,000 lb/hr of combined recycles 12 of $C_2H_6$ and $C_3H_8$ gas feed and $C_4H_{10}$, $C_5H_{12}$ and $C_6H_{14}$ liquids after hydrogenation, are vaporized in vaporizer 14 and mixed with steam in line 16, at a typical weight ratio of about 0.5 steam to hydrocarbons feeds.

The steam helps reduce coking in the tubes of the furnaces, and also reduce the partial pressure of the hydrocarbons, thus increasing ethylene yield.

Figure 3:
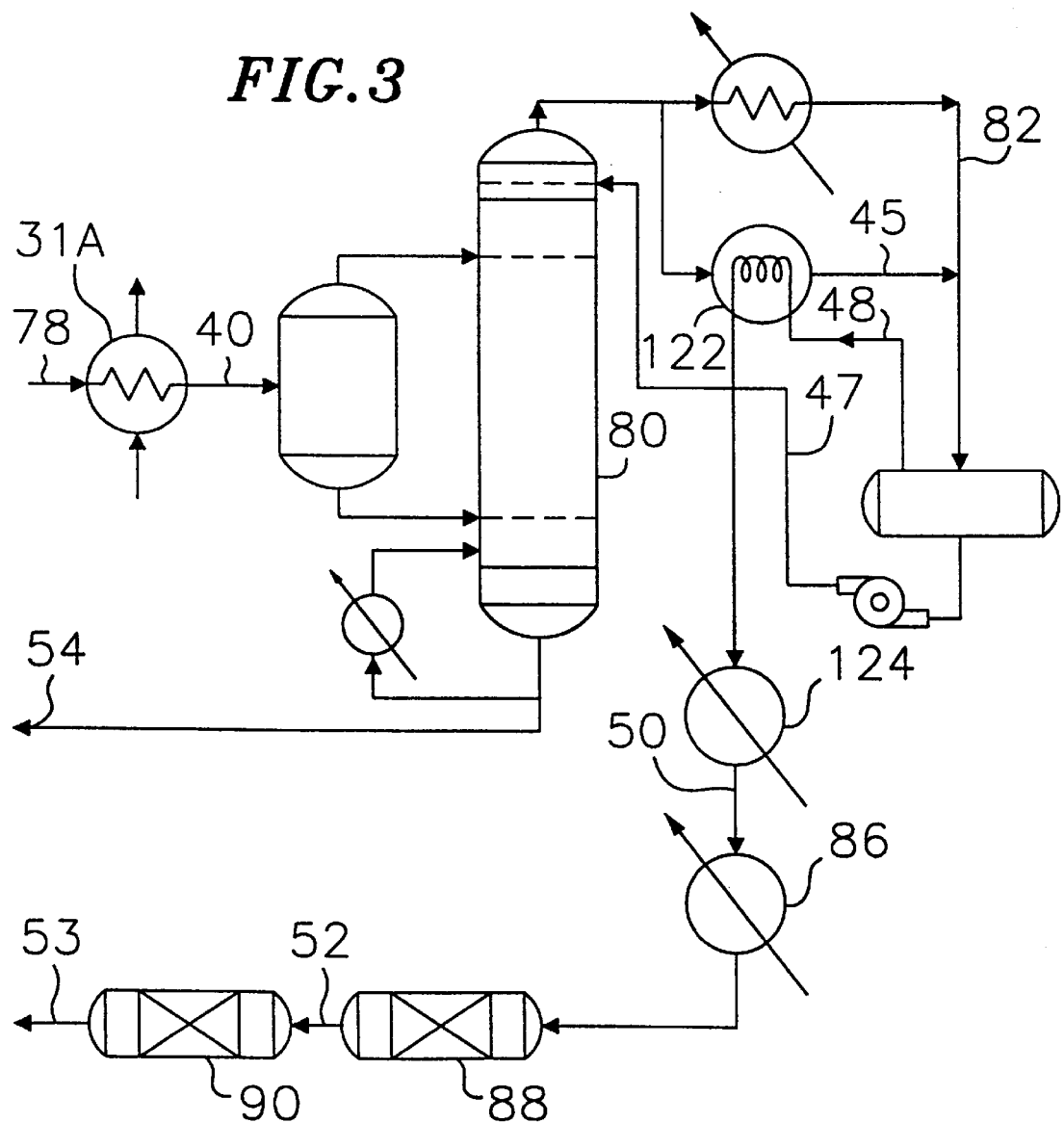
FIG. 3 illustrates the dilute ethylene recovery for use in an adjacent ethylbenzene plant.
Figure 4:
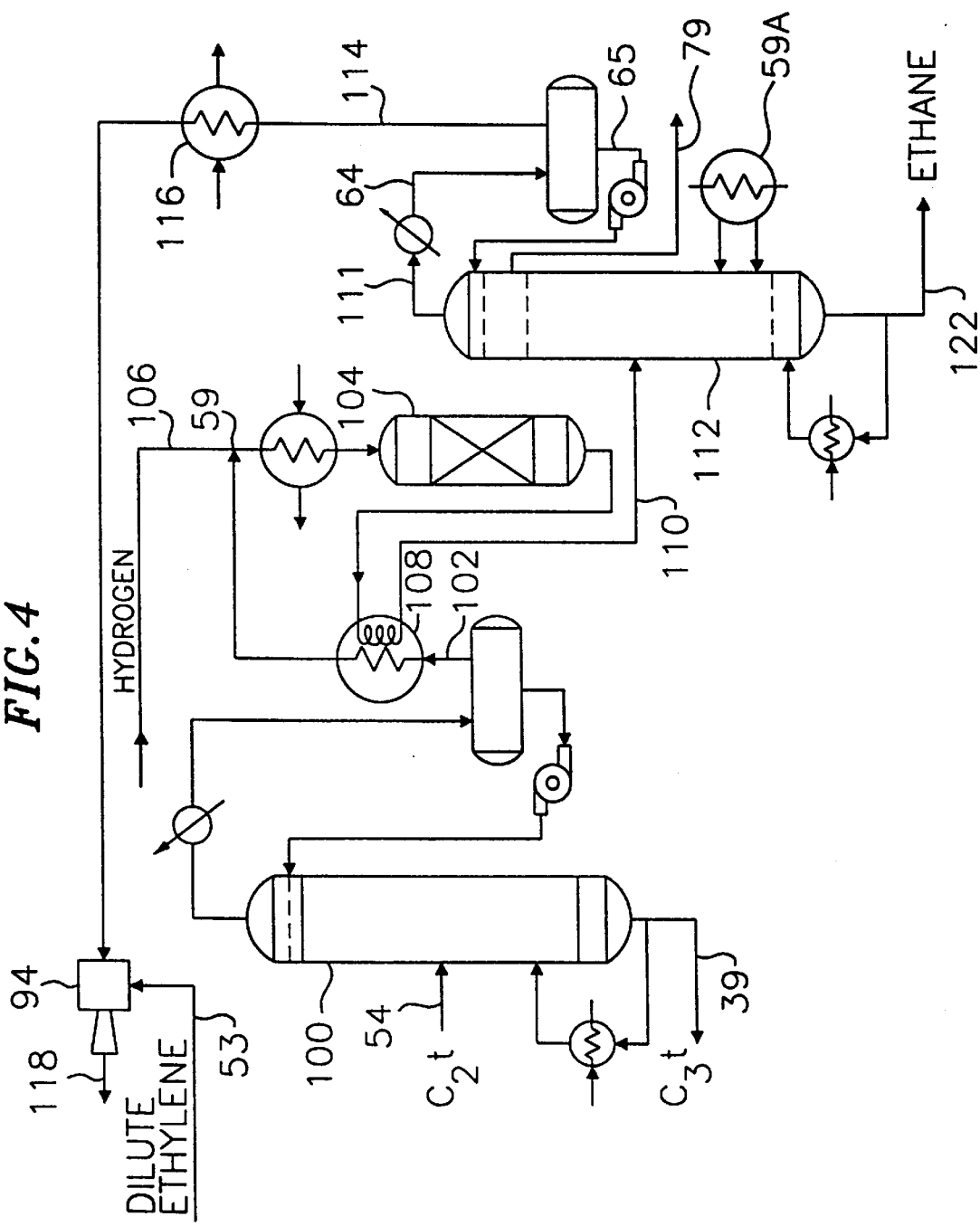
FIG. 4 illustrates the ethylene recovery, acetylene reactor and off specification ethylene diversion to the ethylbenzene plant.

This hydrocarbon steam mixture is further preheated in heater 18 and proceeds, line 20 prior to the cracking section of the pyrolysis furnace 22. The furnace is fired by fuel gas principally $CH_4$ product 24 as recovered from the down stream process. The source of the $CH_4$ with reference to FIG. 3, is the cryogenic separation zone (80) in the ethylene plant. However, its final recovery is from the vent gas 121 in the ethylbenzene plant FIG. 5. For the above naphtha net feed and the recycles, the following typical yield, in weight percent per pass, is shown in Table 1. Hydrodealkylation of toluene in the cracking furnace would further increase benzene and methane production, but will consume hydrogen

TABLE 1

| Component | Wt % | Destination |
|---|---|---|
| Hydrogen | 1.05 | Product to battery limit. (After satisfy internal usage) |
| Methane | 15.8 | Fuel gas product to cracking furnaces |
| Acetylene | 0.9 | Converted to ethylene product |
| Ethylene | 29.6 | Main product to battery limits |
| Ethane | 6.2 | Recycled and converted to ethylene product |
| Propadeine | 0.6 | Converted to propylene product |
| Propylene | 14.0 | Main product to battery limits, or for cumene production |
| Propane | 0.4 | Recycled and converted to products. |

TABLE 1-continued

| Component | Wt % | Destination |
|---|---|---|
| $C_4$ Olefins + Paraffins | 9.5 | Hydrotreated and recycled to cracking |
| $C_5$ Olefins + Paraffins | 4.5 | Hydrotreated and recycled to cracking |
| Benzene | 6.5 | Light gasoline product, feed to ethylbenzene. |
| Toluene | 2.3 | Light gasoline product, a source of benzene by hydrodealkylation |
| Xylene + Ethylbenzene | 0.4 | Heavy gasoline product to battery limits |
| Balance of Pyrolysis Fuel oil and pyrolysis gasoline ($C_6$–$C_{10}$) | 8.1 | Product to battery limit |
| $H_2S$ and $CO_2$ | | Traces waste to battery limits as sodium salts |
| CO | Trace | To fuel |

The net ethylene make is about 5.5 wt % of the naphtha feed in dilute form and about 29.0 wt % of the naphtha feed in concentrated pure form. The net propylene recovery is about 14.5 wt % (before consumption to cumene).

In the heat recovery section 18 of the cracker, hot combustion gas from the pyrolysis section undergoes heat recovery providing preheating boiler feed water 28 and superheating saturated steam 9 at about 1,900 psig and about 650° F. to about 1,800 psig and 980 F. stream 30. The cracked gas 32 is cooled in transfer line exchangers 34 to about 800 to about 840° F. by generating saturated steam at about 1,900 psig and about 650° F. The overall steam production is typically in balance as a motive power source for the cracked gas compression and refrigeration compression drivers of the ethylene plant.

Figure 2:
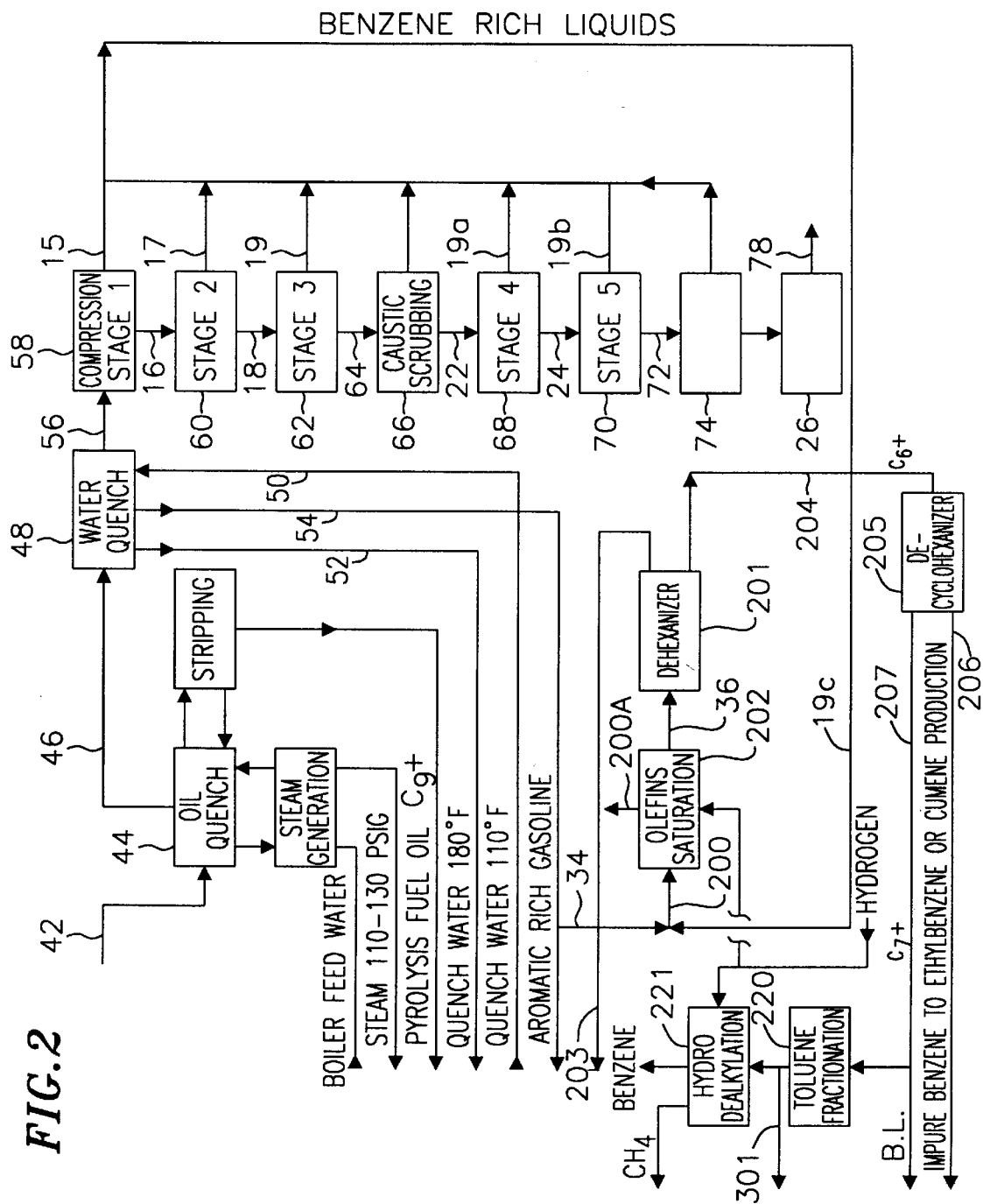
FIG. 2 illustrates the quench oil and quench water pyrolysis gasoline and pyrolysis fuel oil recovery, cracked gas compression, $CO_2$ and $H_2S$ removal, cracked gas drying, pyrolysis gasoline hydrotreating, dehexanizer, benzene recovery, toluene conversion to benzene as a feed to the ethylbenzene plant or cumene plant (not shown).

With reference to FIG. 2, the cracked gas at about 800 to about 840° F. and 10 psig in line 42 after steam generation is quenched with pyrolysis fuel oil in quench zone 44 using oil recycle and heat absorption by generating saturated steam at 110–130 psig.

The net product made after stripping of light pyrolysis products is $C_9$+, pyrolysis fuel oil. The steam at 110–130 psig is ultimately used as a dilution steam for the naphtha and recycle feeds 16. Overhead gas 46 from the quench oil system at about 220–250F. proceeds to the quench water system 48, and preheat quench water at 110° F. in 50 to 180° F. in line 52 and recovery of aromatic rich $C_6$–$C_9$ pyrolysis gasoline 54. The 180° F. water 52 serves as a low level heat source to a number of reboiling services in the plant facility. After utilization of the low level heat, water at about 110° F. is recycled back to the quench water system 48.

Quenched gas is further cooled to about 100° F. with about 88° F. cooling water (depending on ambient conditions) and the bulk of the water vapors and the $C_6$+ products are condensed and separated. The cracked gas at about 5.0 psig proceeds by line 56 to compression. The gas is compressed to about 400–600 psig in four to five stages. For illustration purposes five stages of compression to about 520 psig are assumed. After three stages of compression (58, 60, and 62) to about 140 psig, the gas 64 proceeds to caustic scrubber (66) for $CO_2$ and $H_2S$ removal and further compressed at 68 and 70 to about 520 psig in line 72 and after cooled to about 100° F. The gas is further cooled in exchanger 74 to about $_{60}$° F. by refrigeration or cold recovery prior to water/hydrocarbon separation. The gas proceeds to molecular sieve dryer 26 as needed for downstream cryogenic product recovery. At this point about 99% of the benzene and C$_6$, 85% of the C$_5$ hydrocarbon and 65% of the C$_4$ hydrocarbons are condensed and separated in lines at 15, 17, 19, 19a and 19b and send to raw pyrolysis gasoline 34.

Water and hydrocarbon liquids, mostly C$_4$, C$_5$, and C$_6$ are condensed in the interstage and after stage cooling of the cracked gas compression FIG. 2, stream 15, 17, 19, 19a and also from dryer prechilling (74) and water is separated (not shown). The combined hydrocarbon liquid 19c combines with aromatic rich stream 34 to feed stream 200 to selective olefin and di-olefin saturation unit 202. The hydrotreated stream 36 free of sulfur, proceed to dehexanizer (201) where all C$_4$, C$_5$, and all C$_6$ except cyclohexane and benzene are separated overhead, at an atmospheric cut point of 167° F. This light saturated liquid 200 A recycles back to cracking section 14, (FIG. 1).

Bottom product from 201 fractionation, proceeds to de-cyclohexanizer 205 where benzene, cyclohexane and dimethylpentanes are separated, at an atmospheric cut point of 183° F. The overhead product, stream 206 is impure benzene containing typically 2–8 wt % of cyclohexane and dimethylpentanes and traces of methylcyclopentane and methylcyclohexane. This impure benzene is used as a feed for the ethylbenzene 120 (FIG. 5) or alternately as a feed to a cumene plant, where liquid phase or mixed phase alkylation reactions are employed. Toluene rich stream 207, can proceed to battery limits or alternately to toluene fractionation 220. Overhead toluene proceeds to hydro-dealkylation 221 where hydrogen as formed reacts with toluene to form benzene and methane. As an alternate method, thermal mode of hydrodealkylation will take place in the cracker at about 1600° F. where toluene stream 301 recycles to the naphthe feed stream 10. Over 30% of the toluene per pass is converted to benzene, with an ultimate conversion of over 90%.

With reference to new FIG. 3, about 12710 lb-mol/hr of dry cracked gas at about 500 psig and about 60° F. in line 78 with the molecular composition shown in Table 2, proceeds to a chill down train for cryogenic product recovery.

TABLE 2

| Component | Mol % |
|---|---|
| Hydrogen | 16.9 |
| Methane | 31.8 |
| Acetylene | 0.85 |
| Ethylene | 33.0 |
| Ethane | 5.65 |
| CO | 0.25 |
| Propadiene/ Methyl Acetylene | 0.35 |
| Propylene | 8.90 |
| Propane | 0.45 |
| C$_4$ olefins | 1.40 |
| Butanes | 0.15 |
| C$_5$+ | 0.25 |

In an alternate design (not shown) cracked gas after the 4 stages of compression, at about 270 psig, will go through H$_2$O/CO$_2$ removal, molecular sieve drying and than a chill down for C$_2$/C$_3$ separation in a front end deethanizer. The C$_2$ and lighter fractions are warmed up undergo acetylene hydrogenation to form ethylene and the C$_3$ and heavier hydrocarbon liquids proceed to propylene and C$_4$+ recovery. The acetylene free light gas at about 260 psig is further compressed through the 5th stage to about 520 psig. In yet another alternate design (not shown) the front end separation of the CO$_2$. and lighter hydrocarbons will be carried out at about 500 psig using double fractionation system.

In the primary design, as well as alternate designs, the dry cracked gas at about 500 psig and about 60° F. in line 78 is chilled down to about −200° F. using propylene and ethylene refrigeration, followed by an expander or methane refrigeration (not shown). At this point essentially all the ethylene (99.9%) is condensed in several stages along with the bulk of the methane, and hydrogen rich gas (75% H$_2$) is separated from the crude ethylene liquids which are fed to a demethanizer 80, operating at about 300 to about 500 psig and, for this illustration, preferably about 460 psig. In a conventional design, the overhead product of the demethanizer overhead is essentially methane, some residual hydrogen with very minimal quantity, say 100 vol. ppm, of ethylene. The bottom product 54 is essentially ethylene, ethane, propylene and C$_3$+ hydrocarbons. Methane content is under 100 ppm and hydrogen content is essentially nil. In a conventional design, the ethylene in the overhead of the demethanizer at 48 represents a net ethylene product loss to the fuel gas system, thus a good economical design should minimize its content by appropriate reflux of liquid methane stream 47 at typically about −145° F. The cold for the reflux is provided by ethylene refrigeration at about −150° F. which corresponds to slightly above its atmospheric pressure. Typically 99.8% of the ethylene, and essentially 100% of the ethane and acetylene from the charge gas are recovered as a bottom product for further processing and separation. The same is essentially true for the alternate designs except that essentially no C$_3$+ and acetylene are present in the bottom of the demethanizer.

In the conventional design stream 48 the CH$_4$/H$_2$ overhead from the demethanizer at about 460 psig is typically expanding to fuel gas pressure of about 50 psig in a turbo-expander, (not shown) generating motive power as well as refrigeration (needed for the low temperature ethylene condensation and hydrogen separation). The cold is recovered from the H$_2$/CH$_4$ rich gas prior to diversion to the fuel system for subsequent combustion in the cracking furnaces.

In the instant invention all hydrogen separation occurs in the demethanizer, unless the invention is applied toward revamp of an existing plant. The bottom liquid product 54 of the demethanizer 80 at about 50° F. proceeds is let down to deethanizer 100 operating at about 280 psig. The ethylene, acetylene and ethane are separated as overhead product 102 and propylene and C$_3$+ hydrocarbons as bottom products 39. The overhead product 102 with about 1.9 wt % acetylene is reheated to 130° F. and to passed acetylene hydrogenator 104 with outside hydrogen source 106. The acetylene free, C$_2$ vapor is condensed by preheating the feed in exchange 108 and proceeds to ethylene fractionator 112 at about 240 psig, or lower pressure depending on final disposition of the ethylene product, and the refrigeration system. The above acetylene removal step is not required for the alternate designs, since acetylene is converted upstream of the demethanizer.

The overhead product 114 from the ethylene fractionator 112 is off specification ethylene product. The side draw 79 typically drawn about 8–10 trays below the top in the ethylene fractionator. Residual methane originated from the demethanizer and excess hydrogen from the acetylene converter, are vented (if necessary) from the overhead as off specification ethylene 114.

The off specification ethylene is suitable as a feed to the ethylbenzene plant. The amount of flow after cold recovery in 116 is small. The ethylene is mixed in an ejector 94 with the bulk of the dilute ethylene feed 53 containing about 10% ethylene and about 5 ppm acetylene and propylene, and send to ethylbenzene plant 120. The bottom product 122, essentially ethane is revaporize via cold recovery and sent to the cracking section 14. In the alternate design (not shown), demethanizer bottom proceeds directly to the ethylene fractionator 112. The $C_3+$ hydrocarbon product undergoes separation of $C_3$ and $C_4+$ hydrocarbon (not shown). The $C_3$ product is undergoes hydrogenation of the methyl acetylene and propadiene and proceeds to propylene fractionation (not shown). The overhead product is propylene, the bottom product is propane which is recycled to the cracking section 14.

In the demonstrated case of the invention, the demethanizer is operating in a "sloppy cut" mode, for ethylene and also separate all the hydrogen at the overhead. For illustrative purposes the demethanizer overhead rather than operating with full ethylene recovery at the bottom and essentially no ethylene at the top, has 10 mol % or more ethylene in the overhead and typical propylene content of below 5 ppm by volume. The methane specification for the bottom will be about 100 to about 2,000 mol-ppm. By allowing ethylene to escape from the top, at 10 mol % concentration, about 15% of the ethylene, about 2% of the ethane, and about 8% of the acetylene feeds to the demethanizer, will go overhead. The overhead product gas about 6,890 lb-mol/hr at about −115° F. and about 450 psig will have the approximate molecular composition shown in Table 3:

TABLE 3

| Component | Lb-mol/hr | Mol % |
|---|---|---|
| Hydrogen | 2147 | 31.1 |
| CO | 31 | 0.44 |
| Methane | 4041 | 58.6 |
| Acetylene | 9 | 0.13 |
| Ethylene | 650 | 9.5 |
| Ethane | 13 | 0.19 |
| Propylene | 0.03 | 5 ppm |

With the reference to FIG. 3, the gas is preheated via cold recovery 122 and 124 to about 92° F. and further preheated in exchanger 86 to 130° F. prior to acetylene reactor 88 and then introduced into carbon beds 90. If the acetylene reactor is avoided, the acetylene would react with benzene to form di-phenyl ethane. For the alternate case, these acetylene removal steps are not required. As further optimization, not shown, side reboiler and side condensers can be used for increasing refrigeration economy. Dilute ethylene can be made as a side draw product.

Propylene and acetylene free gas at about 415 psig in line 53 combines with off specification ethylene from ethylene fractionator in ejector 94 and the combined gas 118 proceeds as feed to the ethylation reactor section 120 of the ethylbenzene plant.

Liquids, mostly $C_4$, $C_5$, and $C_6$ as condensed in the gas compression inter and after coolers FIG. 2. 19c combines with 34 to a $C_4$–$C_8$ raw pyrolysis gasoline 200. The raw pyrolysis gasoline is undergoing selective di-olefins and olefins saturation qt. 201. Hydrotreated liquid 36 and $C_6$ boilers below benzene (170° F.) are separated at 202, and sent at 203 for cracking at 14. $C_6+$ stream at 204, is sent to decyclohexanizer 205 where benzene and cyclohexane are separated. The benzene cyclohexane 206, containing over 90 wt % benzene, is used as impure benzene feed to the ethylbenzene plant 120, or to a cumene plant (not shown).

In the ethylbenzene plant 120, ethylene reacts with benzene feed 206 and stoichiometric excess of benzene. The exothermic reaction forms ethylbenzene and poly ethylated benzene (PEB). In a separate trans alkylation reactor 126 the polyethylated benzene reacts with benzene to form ethylbenzene. After series of products fractionation and purifications (128–130), the final products are: (1) Ethylbenzene with purity above 99.5%; (2) Vent gas 132 depleted of 95–99% of the ethylene feed and containing 34.5 mol % of hydrogen; and (3) A small amount, about 0.5–2.0%, of the benzene remains converted to polyethylated product commonly referred to as flux oil (134). The flux oil is routed to pyrolysis fuel oil. The cyclohexane and dimethylpentanes are close boilers to benzene and purged 208 from the benzene recycle loop with 75 wt % benzene. The purge will go to battery limits or to conventional extraction of benzene 212 and benzene 211 will recycle to the feed. The cyclohexane residue 210 will go to battery limits. Additional benzene can be made by separation of toluene. FIG. 2, 220 and conversion of toluene to benzene by hydrodelakylation 221 which is a conventional and known process. However, the conversion by thermal steam cracking in the furnace with co-production of ethylene is an element of the invention. After toluene conversion, the benzene, will be used as make up about 60% of the requirement for the ethylbenzene or cumene production. Without toluene conversion, the benzene will provide about 40% of the alkylated benzene requirement. As an alternative, cyclohexane rich purge 213 will go to benzene hydrogenation for cyclohexane production 214.

Figure 5:
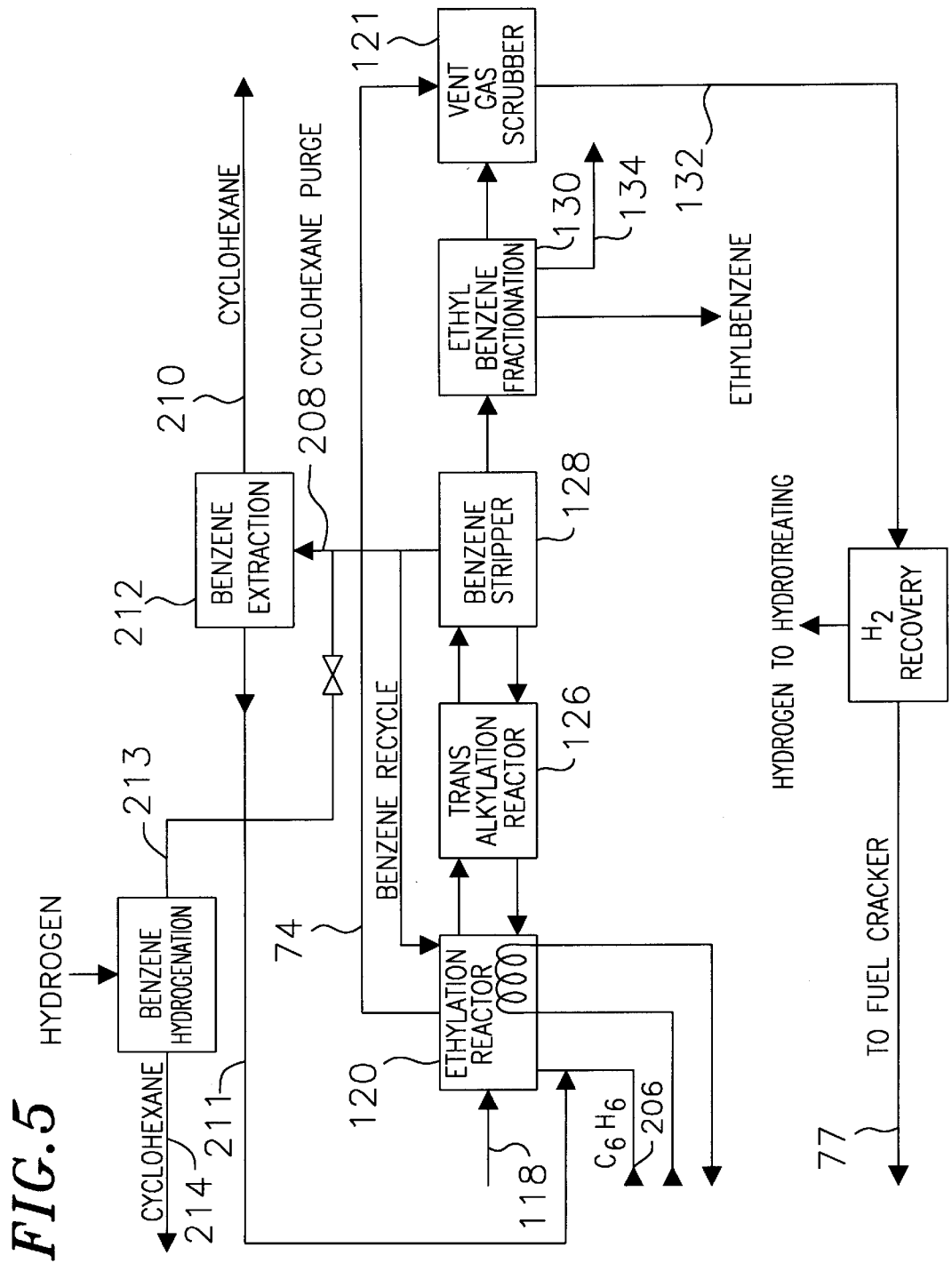
FIG. 5 illustrate ethylbenzene production along with hydrogen recovery.

If high benzene conversion yield is desired, the cyclohexane rich purge 208 can be ethylated in a purge reactor (not shown). The benzene reacts with ethylene to form ethylbenzene and polyethylated benzene. The reaction products will go through a fractionation (not shown). Benzene cyclohexane and other co-boilers will be separated at an atmospheric cut point of about 183° F. Ethylbenzene and polyethylated benzene will be recycled to the trans alkylation reaction 126 (FIG. 5).

What is claimed is:

1. A process for the simultaneous coproduction of ethylbenzene and ethylene comprising:
   (1) producing ethylene and a dilute ethylene mixture containing ethylene and methane and no more than 200 mol-ppm propylene via conventional steam cracking in a steam cracker and downstream propylene separation;
   (2) producing an impure benzene mixture by hydrogenation and fractionation of pyrolysis gasoline during the ethylene production, the impure benzene mixture containing benzene and a total of 1.0 to 20.0 wt % of one or more impurities selected from the group consisting of cyclohexane, dimethylpentanes, methylcyclopentanes and methylcyclohexane;
   (3) feeding impure benzene mixture to an integrated ethylbenzene production zone;
   (4) feeding at least a portion of the dilute ethylene mixture produced during the steam cracking and downstream propylene separation to the ethylbenzene production zone, wherein the ethylene is present in the dilute ethylene mixture in a concentration of about 3 to 40 vol %; and
   (5) reacting the ethylene in the dilute ethylene mixture with the benzene in the impure benzene mixture to form ethylbenzene.

2. A process as claimed in claim 1 in which the impure benzene mixture contains a total of 3.0 to 8.0 wt % of one or more impurities selected from the group consisting of cyclohexane, dimethylpentanes, methylcyclopentanes, and methylcyclohexane.

3. A process as claimed in claim 1, further comprising purging from the ethylbenzene production zone a purged mixture comprising unreacted benzene and a total of 7.0 to 60 wt % of one or more impurities selected from the group consisting of cyclohexane and dimethylpentanes.

4. A process as claimed in claim 1, further comprising purging from the ethylbenzene production zone a purged mixture comprising unreacted benzene and a total of 15.0 to 40.0 wt % of one or more impurities selected from the group consisting of cyclohexane and dimethylpentanes.

5. A process as claimed in claim 1 further comprising:
  a) forming in one or more hydrocarbon cracking zones a cracked gas comprising hydrogen, carbon monoxide, methane, acetylene, ethylene, ethane and propylene and a cracked liquid which includes the pyrolysis gasoline, wherein the pyrolysis gasoline comprises benzene, toluene and cyclohexane;
  b) fractionating said cracked gas in a demethanization zone to form (1) the dilute ethylene mixture wherein the dilute ethylene mixture contains hydrogen, carbon monoxide, methane, and no more than 200 mol-ppm propylene, and ethylene present in an amount of from about 3 to about 35 percent of the ethylene fed to said demethanization zone at a pressure of from about 70 to about 550 psig, whereby the dilute ethylene mixture undergoes no further phase change, and (2) bottoms comprising ethylene and ethane;
  c) reheating the dilute ethylene mixture; and
  d) further purifying the bottoms for ethylene product recovery.

6. A process as claimed in claim 5 in which the demethanization zone is operated at a pressure from 330 to about 550 psig.

7. A process as claimed in claim 5 in which essentially all of the hydrogen in the cracked gas is separated with the dilute ethylene fluid mixture at a temperature above about −150° F. and at pressures of about 300 to about 550 psig.

8. A process according to claim 1 further comprising:
  (a) providing pyrolysis gasoline produced during the steam cracking containing benzene and toluene; and
  (b) converting the toluene to benzene by hydrodealkylation.

9. A process according to claim 1, further comprising converting the ethylbenzene to styrene.

10. A process according to claim 5, further comprising converting the ethylbenzene to styrene.

11. A process according to claim 1, further comprising purifying the ethylbenzene formed in the ethylbenzene production zone to have a purity of at least about 99.5 wt %.

12. A process according to claim 5, further comprising purifying the ethylbenzene formed in the ethylbenzene production zone to have a purity of at least about 99.5 wt %.

* * * * *